United States Patent [19]

Phan et al.

[11] Patent Number: 5,262,007

[45] Date of Patent: Nov. 16, 1993

[54] SOFT ABSORBENT TISSUE PAPER CONTAINING A BIODEGRADABLE QUATERNIZED AMINE-ESTER SOFTENING COMPOUND AND A TEMPORARY WET STRENGTH RESIN

[75] Inventors: Dean V. Phan, West Chester; Bart S. Hersko, Cincinnati, both of Ohio

[73] Assignee: Proctor & Gamble Company, Cincinnati, Ohio

[21] Appl. No.: 865,596

[22] Filed: Apr. 9, 1992

[51] Int. Cl.$^5$ .............................................. D21H 21/22
[52] U.S. Cl. ..................... 162/158; 162/111; 162/112; 162/164.3; 162/164.6; 162/168.2; 162/168.3; 162/179
[58] Field of Search ............ 162/111, 112, 158, 164.1, 162/164.3, 164.6, 168.1, 168.2, 168.3, 179, 169

[56] References Cited

U.S. PATENT DOCUMENTS

| | | | |
|---|---|---|---|
| 2,683,087 | 7/1954 | Reynolds, Jr. | 162/158 |
| 2,683,088 | 7/1954 | Reynolds, Jr. | 162/158 |
| 3,301,746 | 1/1967 | Sanford et al. | 162/113 |
| 3,499,823 | 3/1970 | Croon et al. | 162/158 |
| 3,554,863 | 1/1971 | Hervey et al. | 162/158 |
| 3,755,220 | 8/1973 | Freimark et al. | 260/17.3 |
| 3,817,827 | 6/1974 | Benz | 162/113 |
| 3,844,880 | 10/1974 | Meisel, Jr. et al. | 162/169 |
| 3,974,025 | 8/1976 | Ayers | 162/113 |
| 3,994,771 | 11/1976 | Morgan, Jr. et al. | 162/113 |
| 4,144,122 | 3/1979 | Emanuelsson et al. | 162/158 |
| 4,158,594 | 6/1979 | Becker et al. | 162/158 |
| 4,191,609 | 3/1980 | Trokhan | 162/113 |
| 4,300,981 | 11/1981 | Carstens | 162/109 |
| 4,303,471 | 12/1981 | Laursen | 162/158 |
| 4,351,699 | 9/1982 | Osborn, III | 162/112 |
| 4,377,543 | 3/1983 | Strohbeen et al. | 264/112 |
| 4,425,186 | 1/1984 | May et al. | 162/158 |
| 4,432,833 | 2/1984 | Breese | 162/158 |
| 4,441,962 | 4/1984 | Osborn, III | 162/111 |
| 4,447,294 | 5/1984 | Osborn, III | 162/158 |
| 4,529,480 | 7/1985 | Trokhan | 162/109 |
| 4,637,859 | 1/1987 | Trokhan | 162/109 |
| 4,795,530 | 1/1989 | Soerens et al. | 162/111 |
| 4,853,086 | 8/1989 | Graef | 162/157.6 |
| 4,940,513 | 7/1990 | Spendel | 162/112 |
| 4,959,125 | 9/1990 | Spendel | 162/158 |
| 4,981,557 | 1/1991 | Bjorkquist | 162/168.2 |
| 5,066,414 | 11/1991 | Chang | 252/8.8 |

FOREIGN PATENT DOCUMENTS 61-308312  7/1988  Japan.

OTHER PUBLICATIONS

"Applications of Armak Quaternary Ammonium Salts", Bulletin 76-17, Armak Co., (1977).

*Primary Examiner*—Peter Chin
*Attorney, Agent, or Firm*—Bart S. Hersko; Fredrick H. Braun; E. Kelly Linman

[57] ABSTRACT

Tissue paper webs useful in the manufacture of soft, absorbent products such as napkins, facial tissues, and sanitary tissues, and processes for making the webs. The tissue paper webs comprise papermaking fibers, a biodegradable quaternized amine-ester softening compound, a wetting agent, and a temporary wet strength resin. The process comprises a first step of forming an aqueous papermaking furnish from the above-mentioned components. The second and third steps in the basic process are the deposition of the papermaking furnish onto a foraminous surface such as a Fourdrinier wire and removal of the water from the deposited furnish. An alternate process involves the use of the furnish containing the aforementioned components in a papermaking process which will produce a pattern densified fibrous web having a relatively high bulk field of relatively low fiber density in a patterned array of spaced zones of relatively high fiber density.

3 Claims, No Drawings

SOFT ABSORBENT TISSUE PAPER CONTAINING A BIODEGRADABLE QUATERNIZED AMINE-ESTER SOFTENING COMPOUND AND A TEMPORARY WET STRENGTH RESIN

FIELD OF THE INVENTION

This invention relates to tissue paper webs. More particularly, it relates to soft, absorbent tissue paper webs which can be used in sanitary tissue, facial tissue products, and paper napkins.

BACKGROUND OF THE INVENTION

Paper webs or sheets, sometimes called tissue or paper tissue webs or sheets, find extensive use in modern society. Such items as paper towels, napkins, and facial tissues are staple items of commerce. It has long been recognized that three important physical attributes of these products are their softness; their absorbency, particularly their absorbency for aqueous systems; and their strength, particularly their strength when wet. Research and development efforts have been directed to the improvement of each of these attributes without deleteriously affecting the others as well as to the improvement of two or three attributes simultaneously.

Softness is the tactile sensation perceived by the consumer as he/she holds a particular product, rubs it across his/her skin, or crumples it within his/her hand. This tactile sensation is a combination of several physical properties. One of the more important physical properties related to softness is generally considered by those skilled in the art to be the stiffness of the paper web from which the product is made. Stiffness, in turn, is usually considered to be directly dependent on the dry tensile strength of the web.

Strength is the ability of the product, and its constituent webs, to maintain physical integrity and to resist tearing, bursting, and shredding under use conditions, particularly when wet.

Absorbency is the measure of the ability of a product, and its constituent webs, to absorb quantities of liquid, particularly aqueous solutions or dispersions. Overall absorbency as perceived by the human consumer is generally considered to be a combination of the total quantity of liquid a given mass of tissue paper will absorb at saturation as well as the rate at which the mass absorbs the liquid.

The use of wet strength resins to enhance the strength of a paper web is widely known. For example, Westfelt described a number of such materials and discussed their chemistry in Cellulose Chemistry and Technology, Volume 13, at pages 813–825 (1979).

Freimark et al. in U.S. Pat. No. 3,755,220 issued Aug. 28, 1973 mention that certain chemical additives known as debonding agents interfere with the natural fiber-to-fiber bonding that occurs during sheet formation in papermaking processes. This reduction in bonding leads to a softer, or less harsh, sheet of paper. Freimark et al. go on to teach the use of wet strength resins to enhance the wet strength of the sheet in conjunction with the use of debonding agents to off-set undesirable effects of the debonding agents. These debonding agents do reduce dry tensile strength, but there is also generally a reduction in wet tensile strength.

Shaw, in U.S. Pat. No. 3,821,068, issued Jun. 28, 1974, also teaches that chemical debonders can be used to reduce the stiffness, and thus enhance the softness, of a tissue paper web.

Chemical debonding agents have been disclosed in various references such as U.S. Pat. No. 3,554,862, issued to Hervey et al. on Jan. 12, 1971. These materials include quaternary ammonium salts such as trimethylcocoammonium chloride, trimethyloleylammonium chloride, di(hydrogenated-tallow)dimethylammonium chloride and trimethylstearylammonium chloride.

Emanuelsson et al., in U.S. Pat. No. 4,144,122, issued Mar. 13, 1979, teach the use of complex quaternary ammonium compounds such as bis(alkoxy-(2-hydroxy)-propylene) quaternary ammonium chlorides to soften webs. These authors also attempt to overcome any decrease in absorbency caused by the debonders through the use of nonionic surfactants such as ethylene oxide and propylene oxide adducts of fatty alcohols.

Armak Company, of Chicago, Ill., in their bulletin 76–17 (1977) disclose that the use of di(hydrogenated-tallow)dimethylammonium chloride in combination with fatty acid esters of polyoxyethylene glycols may impart both softness and absorbency to tissue paper webs.

One exemplary result of research directed toward improved paper webs is described in U.S. Pat. No. 3,301,746, issued to Sanford and Sisson on Jan. 31, 1967. Despite the high quality of paper webs made by the process described in this patent, and despite the commercial success of products formed from these webs, research efforts directed to finding improved products have continued.

For example, Becker et al. in U.S. Pat. No. 4,158,594, issued Jan. 19, 1979, describe a method they contend will form a strong, soft, fibrous sheet. More specifically, they teach that the strength of a tissue paper web (which may have been softened by the addition of chemical debonding agents) can be enhanced by adhering, during processing, one surface of the web to a creping surface in a fine patterned arrangement by a bonding material (such as an acrylic latex rubber emulsion, a water soluble resin, or an elastomeric bonding material) which has been adhered to one surface of the web and to the creping surface in the fine patterned arrangement, and creping the web from the creping surface to form a sheet material.

Conventional quaternary ammonium compounds such as the well known dialkyldimethylamonium salts (e.g., ditallowdimethylammonium chloride, ditallowdimethyammonium methylsulfate, di(hydrogenated tallow)dimethyl ammonium chloride, etc.) are effective chemical debonding agents. Unfortunately, these quaternary ammonium compounds are not biodegradable. Applicant has discovered that biodegradable mono- and diester variations of these quaternary ammonium salts also function effectively as chemical debonding agents and enhance the softness of tissue paper webs.

It is an object of this invention to provide a process for making soft, absorbent tissue paper webs with high temporary wet strength.

It is a further object of this invention to provide soft, absorbent tissue paper sheets with high temporary wet strength and that are biodegradable.

It is a still further object of this invention to provide soft, absorbent sanitary tissue products with high temporary wet strength and that are biodegradable.

These and other objects are obtained using the present invention, as will become readily apparent from a reading of the following disclosure.

SUMMARY OF THE INVENTION

The present invention provides soft, absorbent tissue paper webs having high temporary strength, and a process for making the webs. Briefly, the tissue paper webs comprise:

(a) papermaking fibers;

(b) from about 0.01% to about 2.0% by weight of a quaternized amine-ester compound having the formula

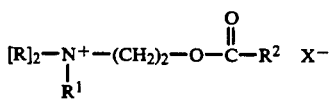

and mixtures thereof; wherein each R substituent is a $C_1$–$C_6$ alkyl or hydroxyalkyl group, or mixtures thereof; $R^1$ is

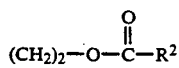

or a $C_{13}$–$C_{19}$ hydrocarbyl group or mixtures thereof; $R^2$ is a $C_{13}$–$C_{21}$ hydrocarbyl group or mixtures thereof; and $X^-$ is a compatible anion;

(c) from about 0.01% to about 2.0% by weight of a wetting agent; and (d) from about 0.01% to about 3.0% by weight of a water-soluble temporary wet strength resin.

Examples of quaternized amine-ester softening compounds suitable for use in the present invention include compounds having the formulas:

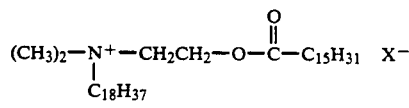
and
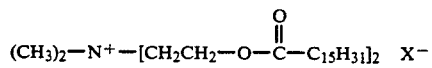

These compounds can be considered to be mono- and di- ester variations of the well-known dialkyldimethylammonium salts such as ditallowdimethylammonium chloride, ditallowdimethylammonium methylsulfate, di(hydrogenated tallow)dimethylammonium chloride, with the diester variations of di(hydrogenated tallow)dimethylammonium methylsulfate and di(hydrogenated tallow)dimethylammonium chloride being preferred. Without being bound by theory, it is believed that the ester moiety(ies) lends biodegradability to these compounds.

Examples of wetting agents useful in the present invention include polyhydroxy compounds such as glycerol and polyethylene glycols having a molecular weight of from about 200 to about 2000, with polyethylene glycols having a molecular weight of from about 200 to about 600 being preferred. Other examples of suitable wetting agents include alkoxylated alcohols, with linear alkoxylated alcohols and linear alkyl phenoxylated alcohols being preferrred.

The temporary wet strength resins useful in the present invention include all those commonly used in papermaking. Examples of preferred temporary wet strength resins include cationic starch-based resins and the cationic polymers described in U.S. Pat. No. 4,981,557, Bjorkquist, issued Jan. 1, 1991.

A particularly preferred tissue paper embodiment of the present invention comprises from about 0.01% to about 0.5% by weight of the quaternized amine-ester softening compound, from about 0.01% to about 0.5% by weight of the wetting agent, and from about 0.1% to about 1.5% by weight of the water-soluble temporary wet strength resin, all quantities of these additives being on a dry fiber weight basis of the tissue paper.

Briefly, the process for making the tissue webs of the present invention comprises the steps of forming a papermaking furnish from the aforementioned components, deposition of the papermaking furnish onto a foraminous surface such as a Fourdrinier wire, and removal of the water from the deposited furnish.

All percentages, ratios and proportions herein are by weight unless otherwise specified.

The present invention is described in more detail below.

DETAILED DESCRIPTION OF THE INVENTION

While this specification concludes with claims particularly pointing out and distinctly claiming the subject matter regarded as the invention, it is believed that the invention can be better understood from a reading of the following detailed description and of the appended examples.

As used herein, the terms tissue paper web, paper web, web, and paper sheet all refer to sheets of paper made by a process comprising the steps of forming an aqueous papermaking furnish, depositing this furnish on a foraminous surface, such as a Fourdrinier wire, and removing the water from the furnish as by gravity or vacuum-assisted drainage, with or without pressing, and by evaporation.

As used herein, an aqueous papermaking furnish is an aqueous slurry of papermaking fibers and the chemicals described hereinafter.

The first step in the process of this invention is the forming of an aqueous papermaking furnish. The furnish comprises papermaking fibers (hereinafter sometimes referred to as wood pulp), at least one wet strength resin, at least one quaternary ammonium and at least one wetting agent, all of which will be hereinafter described.

It is anticipated that wood pulp in all its varieties will normally comprise the papermaking fibers used in this invention. However, other cellulosic fibrous pulps, such as cotton linters, bagasse, rayon, etc., can be used and none are disclaimed. Wood pulps useful herein include chemical pulps such as Kraft, sulfite and sulfate pulps as well as mechanical pulps including for example, ground wood, thermomechanical pulps and chemically modified thermomechanical pulp (CTMP). Pulps derived from both deciduous (e.g., Eucalyptus pulp) and coniferous trees (e.g., spruce) can be used. Also applicable to the present invention are fibers derived from recycled paper, which may contain any or all of the above categories as well as other non-fibrous materials such as fillers and adhesives used to facilitate the original papermaking. Preferably, the papermaking fibers used in this invention comprise Kraft pulp derived from northern softwoods.

Wet Strength Resins

The present invention contains as an essential component from about 0.01% to about 3.0%, more preferably from about 0.1% to about 1.5% by weight, on a dry fiber weight basis, of a water-soluble temporary wet strength resin.

Wet strength resins useful herein can be of several types. Generally, those resins which have previously found and which will hereafter find utility in the papermaking art are useful herein. Numerous examples are shown in the aforementioned paper by Westfelt, incorporated herein by reference.

In the usual case, the wet strength resins are water-soluble, cationic materials. That is to say, the resins are water-soluble at the time they are added to the papermaking furnish. It is quite possible, and even to be expected, that subsequent events such as cross-linking will render the resins insoluble in water. Further, some resins are soluble only under specific conditions, such as over a limited pH range.

Wet strength resins are generally believed to undergo a cross-linking or other curing reactions after they have been deposited on, within, or among the papermaking fibers. Cross-linking or curing does not normally occur so long as substantial amounts of water are present.

Of particular utility are the various polyamide-epichlorohydrin resins. These materials are low molecular weight polymers provided with reactive functional groups such as amino, epoxy, and azetidinium groups. The patent literature is replete with descriptions of processes for making such materials. U.S. Pat. No. 3,700,623, issued to Keim on Oct. 24, 1972 and U.S. Pat. No. 3,772,076, issued to Keim on Nov. 13, 1973 are examples of such patents and both are incorporated herein by reference.

Polyamide-epichlorohydrin resins sold under the trademarks Kymene 557H and Kymene LX by Hercules Incorporated of Wilmington, Del., are particularly useful in this invention. These resins are generally described in the aforementioned patents to Keim.

Base-activated polyamide-epichlorohydrin resins useful in the present invention are sold under the Santo Res trademark, such as Santo Res 31, by Monsanto Company of St. Louis, Mo. These types of materials are generally described in U.S. Pat. Nos. 3,855,158 issued to Petrovich on Dec. 17, 1974; 3,899,388 issued to Petrovich on Aug. 12, 1975; 4,129,528 issued to Petrovich on Dec. 12, 1978; 4,147,586 issued to Petrovich on Apr. 3, 1979; and 4,222,921 issued to Van Eenam on Sep. 16, 1980, all incorporated herein by reference.

Other water-soluble cationic resins useful herein are the polyacrylamide resins such as those sold under the Parez trademark, such as Parez 631NC, by American Cyanamid Company of Stanford, Conn. These materials are generally described in U.S. Pat. Nos. 3,556,932 issued to Coscia et al. on Jan. 19, 1971; and 3,556,933 issued to Williams et al. on Jan. 19, 1971, all incorporated herein by reference.

Other types of water-soluble resins useful in the present invention include acrylic emulsions and anionic styrene-butadiene latexes. Numerous examples of these types of resins are provided in U.S. Pat. No. 3,844,880, Meisel, Jr. et al., issued Oct. 29, 1974, incorporated herein by reference.

Still other water-soluble cationic resins finding utility in this invention are the urea formaldehyde and melamine formaldehyde resins. These polyfunctional, reactive polymers have molecular weights on the order of a few thousand. The more common functional groups include nitrogen containing groups such as amino groups and methylol groups attached to nitrogen.

Although less preferred, polyethylenimine type resins find utility in the present invention.

More complete descriptions of the aforementioned water-soluble resins, including their manufacture, can be found in TAPPI Monograph Series No. 29, *Wet Strength In Paper and Paperboard*, Technical Association of the Pulp and Paper Industry (New York; 1965), incorporated herein by reference.

The above-mentioned wet strength additives typically result in paper products with permanent wet strength, i.e., paper which when placed in an aqueous medium retains a substantial portion of its initial wet strength over time. However, permanent wet strength in some types of paper products can be an unnecessary and undesirable property. Paper products such as toilet tissues, etc., are generally disposed of after brief periods of use into septic systems and the like. Clogging of these systems can result if the paper product permanently retains its hydrolysis-resistant strength properties.

More recently, manufacturers have added temporary wet strength additives to paper products for which wet strength is sufficient for the intended use, but which then decays upon soaking in water. Decay of the wet strength facilitates flow of the paper product through septic systems. As used herein, the term "temporary wet strength resin" refers to a resin that allows the tissue paper, when placed in an aqueous medium, to lose a majority of its initial wet strength in a short period of time, e.g., two minutes or less, more preferably, 30 seconds or less.

Examples of suitable temporary wet strength resins include modified starch temporary wet strength agents such as National Starch 78-0080, marketed by the National Starch and Chemical Corporation (New York, N.Y.). This type of wet strength agent can be made by reacting dimethoxyethyl-N-methyl-chloroacetamide with cationic starch polymers. Modified starch temporary wet strength agents are also described in U.S. Pat. No. 4,675,394, Solarek, et al., issued Jun. 23, 1987, and incorporated herein by reference.

Preferred temporary wet strength resins include those described in U.S. Pat. No. 4,981,557, Bjorkquist, issued Jan. 1, 1991, and incorporated herein by reference. The temporary wet strength resins described in U.S. Pat. No. 4,981,557 comprise a polymer characterized by the substantially complete absence of nucleophilic functionalities and having the formula:

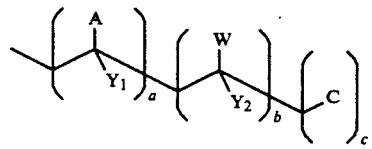

wherein: A is

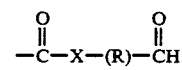

and X is $-O-$, $-NCH_3-$, and R is a substituted or unsubstituted aliphatic groups; $Y_1$ and $Y_2$ are independently $-H$, $-CH_3$ or a halogen; W is a nonnucleophilic, water-soluble nitrogen heterocyclic moiety; C is a cationic monomeric unit; the mole percent of a is from about 30% to about 70%, the mole percent of b is from about 30% to about 70%, and the mole percent of c is from about 1% to about 40%; and said polymer has an average molecular weight of between about 30,000 and about 200,000.

With respect to the classes and specific examples of both permanent and temporary wet strength resins listed above, it should be understood that the resins listed are exemplary in nature and are not meant to limit the scope of this invention.

Mixtures of compatible wet strength resins, such as the temporary wet strength resins described in U.S. Pat. No. 4,981,557 and the modified starch temporary wet strength resins described above, can also be used in the practice of this invention.

Quaternized Amine-Ester Softening Compound

The present invention contains as an essential component from about 0.01% to about 2.0%, more preferably from about 0.01% to about 0.5% by weight, on a dry fiber weight basis, of a quaternized amine-ester softening compound having the formula:

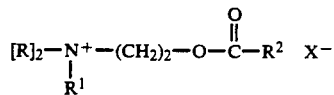

and mixtures thereof; wherein each R substituent is a short chain ($C_1$–$C_6$, preferably $C_1$–$C_3$) alkyl or hydroxyalkyl group, e.g., methyl (most preferred), ethyl, propyl, hydroxyethyl, and the like, or mixtures thereof; $R^1$ is

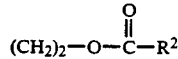

or a long chain $C_{13}$–$C_{19}$ hydrocarbyl substituent, preferably $C_{16}$–$C_{18}$ alkyl, most preferably straight-chain $C_{18}$ alkyl ; $R^2$ is a long chain $C_{13}$–$C_{21}$ hydrocarbyl substituent, preferably $C_{13}$–$C_{17}$ alkyl, most preferably $C_{15}$ straight chain alkyl. The counterion $X^-$ is not critical herein, and can be any softener-compatible anion, such as an halide (e.g., chloride or bromide), or methylsulfate. Preferably, $X^-$ is methyl sulfate or chloride. It will be understood that substituents R, $R^1$ and $R^2$ may optionally be substituted with various groups such as alkoxyl, hydroxyl, or can be branched, but such materials are not preferred herein. The preferred compounds can be considered to be mono- and di- ester variations of the well-known dialkyldimethylammonium salts such as ditallowdimethylammonium chloride, ditallowdimethylammonium methylsulfate, di(hydrogenated tallow)-dimethylammonium chloride, with the diester variations of di(hydrogenatedtallow)dimethylammonium methylsulfate or di(hydrogenated tallow)dimethylammonium chloride being preferred.

Tallow is a naturally occurring material having a variable composition. Swern, Ed. in *Bailey's Industrial Oil and Fat Products*, Third Edition, John Wiley and Sons (New York 1964) in Table 6.13, indicates that typically 78% or more of the fatty acids of tallow contain 16 or 18 carbon atoms. Typically, half of the fatty acids present in tallow are unsaturated, primarily in the form of oleic acid. Synthetic as well as natural "tallows" fall within the scope of the present invention.

The above compounds used as the active softener ingredient in the practice of this invention are prepared using standard reaction chemistry. For example, in a typical synthesis of a monoester variation of a dialkyldimethylammonium salt, an amine of the formula $RR^1NCH_2CH_2OH$ is esterified at the hydroxyl group with an acid chloride of the formula $R^2C(O)Cl$, then quaternized with an alkyl halide, RX, to yield the desired reaction product (wherein R, $R^1$, and $R^2$ are as defined in the present application). A method for the synthesis of a preferred mono-ester softening compound is disclosed in detail hereinafter. However, it will be appreciated by those skilled in the chemical arts that this reaction sequence allows a broad selection of compounds to be prepared. As illustrative, nonlimiting examples there can be mentioned the following quaternized amine monoesters (wherein all long-chain alkyl substituents are straight-chain):

$[CH_3]_2[CH_{18}H_{37}]^+NCH_2CH_2OC(O)C_{15}H_{31}Br^-$
$[CH_3]_2[CH_{13}H_{27}]^+NCH_2CH_2OC(O)C_{17}H_{35}Cl^-$
$[C_2H_5]_2[C_{17}H_{35}]^+NCH_2CH_2OC(O)C_{13}H_{27}Cl^-$
$[C_2H_5][CH_3][C_{18}H_{37}]^+NCH_2CH_2OC(O)C_{14}H_{29}CH_3SO_4^-$
$[C_3H_7][C_2H_5][C_{16}H_{33}]^+NCH_2CH_2OC(O)C_{15}H_{31}Cl^-$
$[iso-C_3H_7][CH_3][CH_{18}H_{37}]^+NCH_2CH_2OC(O)C_{15}H_{31}Cl^-$ Similarly, in a typical synthesis of a diester variation of a dialkyldimethylammonium salt, an amine of the formula $RN(CH_2CH_2OH)_2$ is esterified at both hydroxyl groups with an acid chloride of the formula $R^2C(O)Cl$, then quaternized with an alkyl halide, RX, to yield the desired reaction product (wherein R and $R^2$ are as defined in the present application). A method for the synthesis of a preferred di-ester softening compound is disclosed in detail hereinafter. However, it will be appreciated by those skilled in the chemical arts that this reaction sequence allows a broad selection of compounds to be prepared. As illustrative, nonlimiting examples there can be mentioned the following (wherein all long-chain alkyl substituents are straight-chain):

$[HO-CH(CH_3)CH_2][CH_3]^+N[CH_2CH_2OC(O)C_{15}H_{31}]_2Br^-$
$[C_2H_5]_2^+N[CH_2CH_2OC(O)C_{17}H_{35}]_2Cl^-$
$[CH_3][C_2H_5]^+N[CH_2CH_2OC(O)C_{13}H_{27}]_2I^-$
$[C_3H_7][C_2H_5]^+N[CH_2CH_2OC(O)C_{15}H_{31}]_2SO_4^-CH_3$

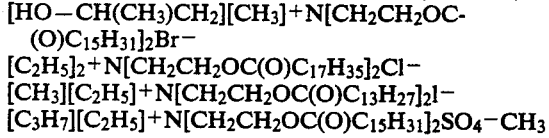

Synthesis of a guaternized amine monoester softening compound

Synthesis of the preferred biodegradable, quaternized amine monoester softening compound used herein is accomplished by the following two-step process:

Step A. Synthesis of Amine

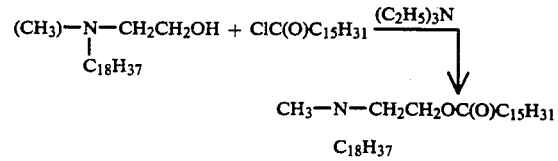

0.6 mole of octadecyl ethanol methyl amine is placed in a 3-liter, 3-necked flask equipped with a reflux condenser, argon (or nitrogen) inlet and two addition funnels. In one addition funnel is placed 0.4 moles of triethylamine and in the second addition funnel is placed 0.6 mole of palmitoyl chloride in a 1:1 solution with methylene chloride. Methylene chloride (750 mL is added to the reaction flask containing the amine and heated to 35° C. (water bath). The triethylamine is added dropwise, and the temperature is raised to 40°–45° C. while stirring over one-half hour. The palmitoyl chloride/methylene chloride solution is added dropwise and allowed to heat at 40°–45° C. under inert atmosphere overnight (12-16 h).

The reaction mixture is cooled to room temperature and diluted with chloroform (1500 mL). The chloroform solution of product is placed in a separatory funnel (4 L) and washed with sat. NaCl, dil. CA(OH)$_2$, 50% K$_2$CO$_3$ (3 times)*, and, finally, sat. NaCl. The organic layer is collected and dried over MgSO$_4$, filtered and solvents are removed via rotary evaporation. Final drying is done under high vacuum (0.25 mm Hg).
*Note: 50% K$_2$CO$_3$ layer will be below chloroform layer.

ANALYSIS

TLC (thin layer chromoatography)**: solvent system (75% diethyl ether: 25% hexane) Rf=0.7.
**10×20 cm prescored glass plates, 250 micron silica gel; visualization by PMA (phosphomolybdic acid - 5% in ethanol) staining.

IR (CCl$_4$): 2910, 2850, 2810, 2760, 1722, 1450, 1370 cm$^{-1}$ $^1$H-NMR (CDCl$_3$): δ2.1-2.5 (8H), 2.1 (3H), 1.20 (58H), 0.9 (6H) ppm (relative to tetramethylsilane=0 ppm).

Step B: Quaternization

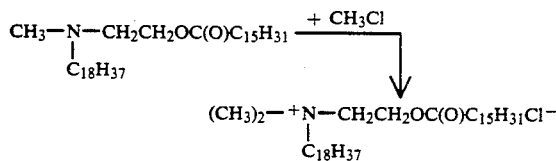

0.5 mole of the octadecyl palmitoyloxyethyl methyl amine, prepared in Step A, is placed in an autoclave sleeve along with 200-300 mL of acetonitrile (anhydrous). The sample is then inserted into the autoclave and purged three times with He (16275 mm Hg/21.4 ATM.) and once with CH$_3$Cl. The reaction is heated to 80° C. under a pressure of 3604 mm Hg/4.7 ATM. CH$_3$Cl and solvent is drained from the reaction mixture. The sample is dissolved in chloroform and solvent is removed by rotary evaporation, followed by drying on high vacuum (0.25 mm Hg). Both the C$_{18}$H$_{37}$ and C$_{15}$H$_{31}$ substituents in this highly preferred compound are n-alkyl.

ANALYSIS

TLC (5:1 chloroform:methanol)*: Rf=0.25.
*10×20 cm prescored glass plates, 250 micron silica gel; visualization by PMA staining.

IR (CCl$_4$): 2910, 2832, 1730, 1450 cm$^{-1}$.

$^1$H-NMR (CDCl$_3$): δ4.0-4.5 (2H), 3.5 (6H), 2.0-2.7 (6H), 1.2-1.5 (58H), 0.9 (6H) ppm (relative to tetramethylsilane=0 ppm).

$^{13}$C-NMR (CDCl$_3$) δ172.5, 65.3, 62.1, 57.4, 51.8, 33.9, 31.8, 29.5, 28.7, 26.2, 22.8, 22.5, 14.0 (relative to tetramethylsilane=0 ppm).

Synthesis of a guaternized amine di-ester softening compound

The preferred biodegradable, quaternized amine diester fabric softening compound used in the present invention may be synthesized using the following two-step process:

Step A. Synthesis of Amine

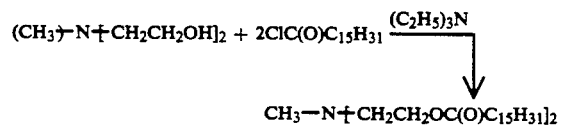

0.6 mole of methyl diethanol amine is placed in a 3-liter, 3-necked flask equipped with a reflux condenser, argon (or nitrogen) inlet and two addition funnels. In one addition funnel is placed 0.8 moles of triethylamine and in the second addition funnel is placed 1.2 moles of palmitoyl chloride in a 1:1 solution with methylene chloride. Methylene chloride (750 mL) is added to the reaction flask containing the amine and heated to about 35° C. (water bath). The triethylamine is added dropwise, and the temperature is raised to 40°–45° C. while stirring over one-half hour. The palmitoyl chloride/methylene chloride solution is added dropwise and allowed to heat at 40°–45° C. under inert atmosphere overnight (12-16 h).

The reaction mixture is cooled to room temperature and diluted with chloroform (1500 ml). The chloroform solution of product is placed in a separatory funnel (4 L) and washed with sat. NaCl, dil. CA(OH)$_2$, 50% K$_2$CO$_3$ (3 times)*, and, finally, sat. NaCl. The organic layer is collected and dried over MgSO$_4$ and filtered. Solvents are removed via rotary evaoporation. Final drying is done under high vacuum (0.25 mm Hg).
*Note: 50% K$_2$CO$_3$ layer will be below chloroform layer.

ANALYSIS

TLC (thin layer chromatography)**: solvent system (75% diethyl ether: 25% hexane) Rf=0.75.
**10×20 cm prescored glass plates, 250 micron silica gel; visualization by PMA (phosphomolybdic acid—5% in ethanol) staining.

IR (CCl$_4$): 2920, 2850, 1735, 1450, 1155, 1100 cm$^{-1}$.

$^1$H-NMR (CDCl$_3$): δ3.9-4.1 (2H), 2.1-2.8 (8H), 2.3 (3H), 1.25 (52H), 1.1 (6H), 0.8 (6H) ppm (relative to tetramethylsilane=0 ppm).

Step B: Ouaternization

Step B: Quaternization

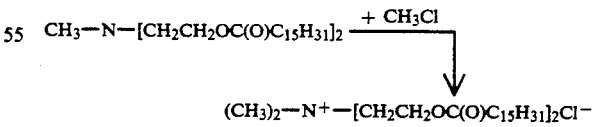

0.5 moles of the methyl diethanol palmitate amine from Step A is placed in an autoclave sleeve along with 200-300 mL of acetonitrile (anhydous). The sample is then inserted into the autoclave and purged three times with He (16275 mm Hg/21.4 ATM.) and once with CH$_3$Cl. The reaction is heated to 80° C. under a pressure of 3604 mm Hg/4.7 ATM. CH$_3$Cl for 24 hours. The autoclave sleeve is then removed from the reaction mixture. The sample is dissolved in chloroform and solvent is removed by rotary evaporation, followed by drying on high vacuum (0.25 mm Hg).

ANALYSIS

TLC (5:1 chloroform:methanol)*: Rf=0.35.
10×20 cm prescored glass plates, 250 microns silica gel; visualization by PMA staining.

IR (CCl$_4$): 2915, 2855, 1735, 1455, 1150 cm$^{-1}$.

$^1$H-NMR (CDCl$_3$): δ4.5–5.0 (2H), 4.0–4.4 (4H), 3.7 (6H), 2.0–2.5 (4H), 1.2–1.5 (52H), 0.9 (6H) ppm (relative to tetramethylsilane=0 ppm).

$^{13}$C-NMR (CDCl$_3$); δ172.8, 63.5, 57.9, 52.3, 33.8, 31.8, 31.4, 29.62 24.6, 22.6, 14.1 ppm (relative to tetramethylsilane=0 ppm).

Although one skilled in the art can prepare the active softener ingredient using standard reaction chemistry, as illustrated above, various quaternized amine-ester compounds are also available commercially under the tradenames SYNPROLAM FS from ICI and REWOQUAT from REWO. A preferred quaternized amine-ester softening compound, i.e., the diester of di(hydrogenated tallow)dimethyl ammonium chloride, is available commercially from the Sherex Chemical Company Inc. of Dublin, Ohio under the tradename "Adogen DDMC".

Wetting Agent

The present invention contains as an essential component from 0.01% to about 2.0%, more preferably from about 0.01% to about 0.5% by weight, on a dry fiber weight basis, of a wetting agent.

Examples of wetting agents useful in the present invention include polyhydroxy compounds such as glycerol and polyethylene glycols having a molecular weight of from about 200 to about 2000, with polyethylene glycols having a molecular weight of from about 200 to about 600 being preferred.

A particularly preferred polyhydroxy wetting agent is polyethylene glycol having a molecular weight of about 400. This material is available commercially from the Union Carbide Company of Danbury, Conn. under the tradename "PEG-400".

Other types of wetting agents useful in the present invention include alkoxylated alcohols. Preferably, the alkoxylated alcohol wetting agents are selected from the group consisting of linear alkoxylated alcohols, linear alkyl phenoxylated alcohols, and mixtures thereof. Most preferably, the alkoxylated is a linear ethoxylated alcohol or a linear alkyl phenoxypoly(ethyleneoxy) alcohol.

Specific linear ethoxylated alcohols useful in the present invention are selected from the group consisting of the condensation products of C$_8$–C$_{18}$ linear fatty alcohols with from about 1 to 10 moles of ethylene oxide and mixtures thereof. Examples of linear ethoxylated alcohols of this type include Neodol 23-3 (the condensation product of C$_{12}$–C$_{13}$ linear alcohol with 3 moles ethylene exide), Neodol 91-2.5 (the condensation product of C$_9$–C$_{11}$ linear alcohol with 2.5 moles ethylene oxide), Neodol 45-9 (the condensation product of C$_{14}$–C$_{15}$ linear alcohol with 9 moles ethylene oxide), Neodol 45-7 (the condensation product of C$_{14}$–C$_{15}$ linear alcohol with 7 moles ethylene oxide), Neodol 45-4 (the condensation product of C$_{14}$–C$_{15}$ linear alcohol with 4 moles ethylene oxide), all of which are marketed by Shell Chemical Company. Preferred are the condensation products of C$_{10}$–C$_{15}$ linear alcohols with from about 4 to 8 moles of ethylene oxide, most preferred are the condensation products of C$_{12}$–C$_{13}$ linear alcohols with 7 moles ethylene oxide (e.g., Neodol 23-7).

Specific linear alkyl phenoxypoly(ethyleneoxy) alcohols useful in the present invention are selected from the group consisting of the condensation products of C$_8$–C$_{18}$ alkyl phenoxy fatty alcohols with from about 1 to 10 moles of ethylene oxide and mixtures thereof. Examples of alkyl phenoxypoly(ethyleneoxy) alcohols of this type include Igepal RC-520, Igepal RC-620, Igepal DM-530, Igepal CTA-639W, all of which are marketed by the Rhone Poulenc Corporation (Cranbury, N.J.). Most preferred are Igepal RC-520 and RC-620.

Optional Ingredients

Other chemicals commonly used in papermaking can be added to the papermaking furnish so long as they do not significantly and adversely affect the softening, absorbency, and wet strength enhancing actions of the three required chemicals.

For example, surfactants may be used to treat the tissue paper webs of the present invention. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as Crodesta TM SL-40 which is available from Croda, Inc. (New York, N.Y.); alkylglycoside ethers as described in U.S. Pat. No. 4,011,389, issued to W. K. Langdon, et al. on Mar. 8, 1977.

Other types of chemicals which may be added include dry strength additives to increase the tensile strength of the tissue webs. Examples of dry strength additives include cationic polymers from the ACCO chemical family such as ACCO 771 and ACCO 514. The level of dry strength additive, if used, is preferably from about 0.01% to about 1.0%, by weight, based on the dry fiber weight of the tissue paper.

The above listings of additional chemical additives is intended to be merely exemplary in nature, and are not meant to limit the scope of the invention.

The papermaking furnish can be readily formed or prepared by mixing techniques and equipment well known to those skilled in the papermaking art.

The three types of chemical ingredients described above, i.e., quaternized amine-ester softening compounds, wetting agents, and water soluble temporary wet strength resins, are preferably added to the aqueous slurry of papermaking fibers, or furnish in the wet end of the papermaking machine at some suitable point ahead of the Fourdrinier wire or sheet forming stage. However, applications of the above chemical ingredients subsequent to formation of a wet tissue web and prior to drying of the web to completion will also provide significant softness, absorbency, and wet strength benefits and are expressly included within the scope of the present invention.

It has been discovered that the chemical ingredients are more effective when the quaternized amine-ester compound and the wetting agent are first premixed together before being added to the papermaking furnish. A preferred method, as will be described in greater detail hereinafter in Example 1, consists of first heating the wetting agent to a temperature of about 180° F., and then adding the quaternized amine-ester compound to the hot wetting agent to form a fluidized "melt". Preferably, the molar ratio of the quaternized amine-ester compound to the wetting agent is about 1 to 1, although this ratio will vary depending upon the molecular weight of the particular wetting agent and/or quaternized amine-ester compound used. The quaternized amine-ester compound and wetting agent melt is then diluted to the desired concentration, and mixed to form an aqueous vesicle solution which is then added to the papermaking furnish.

Since the quaternized amine-ester compounds (both mono- and di-esters) are somewhat labile to hydrolysis, they should be handled rather carefully when diluted to the desired concentrations. For example, stable diluted liquid compositions herein are formulated at a pH in the range of about 2.0 to about 5.0, preferably about pH $3.0\pm0.5$. The pH can be adjusted by the addition of a Bronsted acid. Examples of suitable Bronsted acids include the inorganic mineral acids, carboxylic acids, in particular the low molecular weight ($C_1$–$C_5$) carboxylic acids, and alkylsulfonic acids. Suitable inorganic acids include HCl, $H_2SO_4$, $HNO_3$ and $H_3PO_4$. Suitable organic acids include formic, acetic, methylsulfonic and ethylsulfonic acid. Preferred acids are hydrochloric and phosphoric acids.

Without being bound by theory, it is believed that the wetting agent enhances the flexibility of the cellulosic fibers, improves the absorbency of the fibers, and acts to stabilize the quaternized amine-ester compound in the aqueous solution. Separately, the temporary wet strength resins are also diluted to the appropriate concentration and added to the papermaking furnish. The quaternized amine-ester/wetting agent chemical softening composition acts to make the paper product soft and absorbent, while the temporary wet strength resin insures that the resulting paper product also has high temporary wet strength. In other words, the present invention makes it possible to not only improve both the softness and absorbent rate of the tissue webs, but also provides a high level of temporary wet strength.

The second step in the process of this invention is the depositing of the papermaking furnish on a foraminous surface and the third is the removing of the water from the furnish so deposited. Techniques and equipment which can be used to accomplish these two processing steps will be readily apparent to those skilled in the papermaking art.

The present invention is applicable to tissue paper in general, including but not limited to conventionally felt-pressed tissue paper; pattern densified tissue paper such as exemplified in the aforementioned U.S. Patent by Sanford-Sisson and its progeny; and high bulk, uncompacted tissue paper such as exemplified by U.S. Pat. No. 3,812,000, Salvucci, Jr., issued May 21, 1974. The tissue paper may be of a homogenous or multilayered construction; and tissue paper products made therefrom may be of a single-ply or multi-ply construction. The tissue paper preferably has a basis weight of between 10 $g/m^2$ and about 65 $g/m^2$, and density of about 0.60 g/cc or less. More preferably, basis weight will be below about 35 $g/m^2$ or less; and density will be about 0.30 g/cc or less. Most preferably, density will be between 0.04 g/cc and about 0.20 g/cc.

Conventionally pressed tissue paper and methods for making such paper are known in the art. Such paper is typically made by depositing the papermaking furnish on a foraminous forming wire. This forming wire is often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided in a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a stream drum apparatus known in the art as a Yankee dryer. Pressure can be developed at the Yankee dryer by mechanical means such as an opposing cylindrical drum pressing against the web. Multiple Yankee dryer drums may be employed, whereby additional pressing is optionally incurred between the drums. The tissue paper structures which are formed are referred to hereinafter as conventional, pressed, tissue paper structures. Such sheets are considered to be compacted since the web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones may be discretely spaced within the high bulk field or may be interconnected within the high bulk field. Preferred processes for making pattern densified tissue webs are disclosed in U.S. Pat. No. 3,301,746, issued to Sanford and Sisson on Jan. 31, 1967, U.S. Pat. No. 3,974,025, issued to Peter G. Ayers on Aug. 10, 1976, and U.S. Pat. No. 4,191,609, issued to Paul D. Trokhan on Mar. 4, 1980, and U.S. Pat. No. 4,637,859, issued to Paul D. Trokhan on Jan. 20, 1987; all of which are incorporated herein by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further dedensified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones may be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned placement of knuckles which operate as the array of supports which facilitate the formation of the densified zones upon application of pressure. The pattern of knuckles constitutes the array of supports previously referred to. Imprinting carrier fabrics are disclosed in U.S. Pat. No. 3,301,746, Sanford and Sisson, issued Jan. 31, 1967, U.S. Pat. No. 3,821,068, Salvucci, Jr. et al., issued May 21, 1974, U.S. Pat. No. 3,974,025, Ayers, issued Aug. 10, 1976, U.S. Pat. No. 3,573,164, Friedberg et al., issued Mar. 30, 1971, U.S. Pat. No. 3,473,576, Amneus, issued Oct. 21, 1969, U.S. Pat. No. 4,239,065, Trokhan, issued Dec. 16, 1980, and U.S. Pat. No. 4,528,239, Trokhan, issued Jul. 9, 1985, all of which are incorporated herein by reference.

Preferably, the furnish is first formed into a wet web on a foraminous forming carrier, such as a Fourdrinier wire. The web is dewatered and transferred to an imprinting fabric. The furnish may alternately be initially deposited on a foraminous supporting carrier which also operates as an imprinting fabric. Once formed, the wet web is dewatered and, preferably, thermally pre-dried to a selected fiber consistency of between about 40% and about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll which supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure may be applied to induce impression of densified zones during initial dewatering, in a separate, subsequent process stage, or a combination thereof.

Uncompacted, nonpattern-densified tissue paper structures are described in U.S. Pat. No. 3,812,000 issued to Joseph L. Salvucci, Jr. and Peter N. Yiannos on May 21, 1974 and U.S. Pat. No. 4,208,459, issued to Henry E. Becker, Albert L. McConnell, and Richard Schutte on Jun. 17, 1980, both of which are incorporated herein by reference. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least 80%, and creping the web. Water is removed from the web by vacuum dewatering and thermal drying. The resulting structure is a soft but weak high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25–50%, transferring the web to a thermal dryer such as a Yankee and creping the web. Overall, water is removed from the web by vacuum, mechanical pressing and thermal means. The resulting structure is strong and generally of singular density, but very low in bulk, absorbency and in softness.

The tissue paper web of this invention can be used in any application where soft, absorbent tissue paper webs with high temporary wet strength are required. One particularly advantageous use of the tissue paper web of this invention is in sanitary tissue products (e.g., toilet paper).

Analysis of the amount of treatment chemicals herein retained on tissue paper webs can be performed by any method accepted in the applicable art. For example, the level of the quaternized amine-ester compound, such as an ester variation of a dialkyldimethylammonium salt, retained by the tissue paper can be determined by solvent extraction of the compound by an organic solvent followed by an anionic/cationic titration using Dimidium Bromide as indicator; the level of the wetting agent, such as PEG-400, can be determined by extraction in an organic solvent followed by gas chromatography to determine the level of PEG-400 in the extract; the level of temporary wet strength resin such as a temporary wet strength resin with a nitrogen moiety (e.g., as described in U.S. Pat. No. 4,981,557, D. W. Bjorkquist issued Jan. 1, 1991) resin can be determined by subtraction from the total nitrogen level obtained via the Nitrogen Analyzer, the amount of quaternized amine-ester compound level, determined by the above titration method. These methods are exemplary, and are not meant to exclude other methods which may be useful for determining levels of particular components retained by the tissue paper.

Hydrophilicity of tissue paper refers, in general, to the propensity of the tissue paper to be wetted with water. Hydrophilicity of tissue paper may be somewhat quantified by determining the period of time required for dry tissue paper to become completely wetted with water. This period of time is referred to as "wetting time." In order to provide a consistent and repeatable test for wetting time, the following procedure may be used for wetting time determinations: first, a conditioned sample unit sheet (the environmental conditions for testing of paper samples are $23° \pm 1°$ C. and $50 \pm 2\%$ RH. as specified in TAPPI Method T 402), approximately $4\frac{3}{8}$ inch $\times 4\frac{3}{4}$ inch (about 11.1 cm $\times$ 12 cm) of tissue paper structure is provided; second, the sheet is folded into four (4) juxtaposed quarters, and then crumpled into a ball approximately 0.75 inches (about 1.9 cm) to about 1 inch (about 2.5 cm) in diameter; third, the balled sheet is placed on the surface of a body of distilled water at $23° \pm 1°$ C. and a timer is simultaneously started; fourth, the timer is stopped and read when wetting of the balled sheet is completed. Complete wetting is observed visually.

The preferred hydrophilicity of tissue paper depends upon its intended end use. It is desirable for tissue paper used in a variety of applications, e.g., toilet paper, to completely wet in a relatively short period of time to prevent clogging once the toilet is flushed. Preferably, wetting time is 2 minutes or less. More preferably, wetting time is 30 seconds or less. Most preferably, wetting time is 10 seconds or less.

Hydrophilicity characters of tissue paper embodiments of the present invention may, of course, be determined immediately after manufacture. However, substantial increases in hydrophobicity may occur during the first two weeks after the tissue paper is made: i.e., after the paper has aged two (2) weeks following its manufacture. Thus, the above stated wetting times are preferably measured at the end of such two week period. Accordingly, wetting times measured at the end of a two week aging period at room temperature are referred to as "two week wetting times."

The density of tissue paper, as that term is used herein, is the average density calculated as the basis weight of that paper divided by the caliper, with the appropriate unit conversions incorporated therein. Caliper of the tissue paper, as used herein, is the thickness of the paper when subjected to a compressive load of 95 $g/in^2$ (14.7 $g/cm^2$).

The following examples illustrate the practice of the present invention but is not intended to be limiting thereof.

EXAMPLE 1

The purpose of this example is to illustrate one method that can be used to make soft, absorbent and high temporary wet strength tissue fibrous structure treated with a mixture of Diester Dihydrogenated Tallow Dimethyl Ammonium Chloride (DEDTDMAC)- (i.e., ADOGEN DDMC from the Sherex Chemical Company) and a polyethylene glycol wetting agent (i.e., PEG-400 from the Union Carbide Company) in the presence of a temporary wet strength resin in accordance with the present invention.

A pilot scale Fourdrinier papermaking machine is used in the practice of the present invention. First, a 1% solution of the chemical softener composition containing DEDTDMAC and PEG-400 is prepared according to the following procedure: 1 . An equivalent molar concentration of DEDTDMAC and PEG-400 is weighed; 2. PEG is heated up to about 180° F.; 3. DEDTDMAC is dissolved into PEG to form a melted solution; 4. Shear stress is applied to form a homogeneous mixture of DEDTDMAC in PEG; 5. The pH of the dilution water is adjusted to about 3 by the addition of hydrochloric acid. 6. The dilution water is then heated up to about 180° F.; 7. The melted mixture of DEDTDMAC/PEG-400 is diluted to a 1% solution; and 8. Shear stress is applied to form an aqueous solution containing a vesicle suspension of the DEDTDMAC/PEG-400 mixture.

Second, a 3% by weight aqueous slurry of NSK is made up in a conventional re-pulper. The NSK slurry is refined gently and a 2% solution of the temporary wet strength resin (as described in U.S. Pat. No. 4,981,557, D. W. Bjorkquist issued Jan. 1, 1991) is added to the NSK stock pipe at a rate of 0.75% by weight of the dry fibers. The adsorption of the temporary wet strength resin onto NSK fibers is enhanced via an in-line mixer. The NSK slurry is diluted to about 0.2% consistency at the fan pump.

Third, a 3% by weight aqueous slurry of Eucalyptus fibers is made up in a conventional re-pulper. A 1% solution of the chemical softener mixture is added to the Eucalyptus stock pipe before the stock pump at a rate of 0.2% by weight of the dry fibers. The adsorption of the chemical softener mixture to the Eucalyptus fibers can be enhanced via an in-line mixer. The Eucalyptus slurry is diluted to about 0.2% consistency at the fan pump.

The treated furnish mixture (30% of NSK/70% of Eucalyptus) is blended in the head box and deposited onto a Fourdrinier wire to form an embryonic web. Dewatering occurs through the Fourdrinier wire and is assisted by a deflector and vacuum boxes. The Fourdrinier wire is of a 5-shed, satin weave configuration having 87 machine-direction and 76 cross-machine-direction monofilaments per inch, respectively. The embryonic wet web is transferred from the Fourdrinier wire, at a fiber consistency of about 15% at the point of transfer, to a photo-polymer belt having 562 Linear Idaho cells per square inch, 32 percent of knuckle areas and 6 mils of photo-polymer depth. Further dewatering is accomplished by vacuum assisted drainage until the web has a fiber consistency of about 28%. The patterned web is predried by air blow-through to a fiber consistency of about 65% by weight. The web is then adhered to the surface of a Yankee dryer with a sprayed creping adhesive comprising 0.25% aqueous solution of Polyvinyl Alcohol (PVA). The fiber consistency is increased to an estimated 98% before the dry creping the web with a doctor blade. The doctor blade has a bevel angle of about 24 degrees and is positioned with respect to the Yankee dryer to provide an impact angle of about 83 degrees; the Yankee dryer is operated at about 800 fpm (feet per minute) (about 244 meters per minute). The dry web is formed into roll at a speed of 700 fpm (214 meters per minute).

Two plies of the web are formed into tissue paper products and laminating together using conventional ply bonding techniques well known in the papermaking industry. The tissue paper has about 23 lbs./1000 sq. ft. basis weight, contains about 0.05% of DEDTDMAC, 0.05% PEG-400, and about 0.5% of the temporary wet strength resin. Importantly, the resulting tissue paper is soft, absorbent and has high temporary wet strength.

EXAMPLE 2

The purpose of this example is to illustrate one method that can be used to make soft, absorbent and high temporary wet strength tissue fibrous structure treated with a mixture of Diester Dihydrogenated Tallow Dimethyl Ammonium Chloride (DEDTDMAC) and a linear ethoxylated alcohol wetting agent (i.e., Neodol 23-7 from the Shell Chemical Company) in the presence of a temporary wet strength resin in accordance with the present invention.

The tissue structure is produced in accordance with the hereinbefore described process of Example 1 with the exception that an equivalent molar concentration of Neodol 23-7 is used as the wetting agent instead of PEG-400. The resulting tissue paper contains about 0.05% DEDTDMAC, 0.05% Neodol 23-7, and about 0.5% of the temporary wet strength. Importantly, the tissue paper is soft, absorbent and has high temporary wet strength.

EXAMPLE 3

The purpose of this example is to illustrate one method that can be used to make soft, absorbent and high temporary wet strength tissue fibrous structure treated with a mixture of Diester Dihydrogenated Tallow Dimethyl Ammonium Chloride (DEDTDMAC)

and a linear alkylphenoxypoly(ethyleneoxy) alcohol (Igepal RC-520) in the presence of a temporary wet strength resin in accordance with the present invention.

The tissue structure is produced in accordance with the hereinbefore described process of Example 1 with the exception that an equivalent molar concentration of Igepal RC-520 (a linear dodecylphenoxypoly(ethyleneoxy) alcohol with about 5 moles ethylene oxide per mole of dodecylphenol) is used as the wetting agent instead of PEG-400. The resulting tissue paper contains about 0.05% DEDTDMAC, 0.05% Igepal RC-520, and about 0.5% of the temporary wet strength. Importantly, the tissue paper is soft, absorbent and has high temporary wet strength.

What is claimed is:

1. A strong, soft, absorbent biodegradable tissue paper web comprising:
   (a) papermaking fibers;
   (b) from about 0.01% to about 2.0% by weight of a biodegradable quaternized amine-ester softening compound having the formula

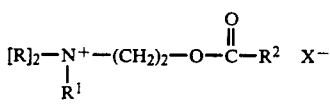

and mixtures thereof; wherein each R substituent is a $C_1$-$C_6$ alkyl or hydroxyalkyl group, or mixtures thereof; $R^1$ is

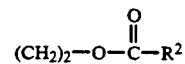

or a $C_{13}$-$C_{19}$ hydrocarbyl group or mixtures thereof; $R^2$ is a $C_{13}$-$C_{21}$ hydrocarbyl group, or mixtures thereof; and $X^-$ is a compatible anion;
   (c) from about 0.01% to about 2.0% by weight of a polyhydroxy compound selected from the group consisting of glycerol and polyethylene glycols having a molecular weight from about 200 to about 2000; and
   (d) from about 0.01% to about 3.0% by weight of a water-soluble temporary wet strength resin.

2. The paper web of claim 1 wherein said polyhydroxy compound is a polyethylene glycol having a molecular weight from about 200 to about 600.

3. The paper web of claim 2 wherein said quaternized amine-ester softening compound is

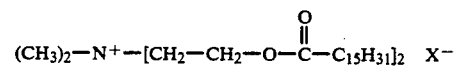

* * * * *

UNITED STATES PATENT AND TRADEMARK OFFICE
CERTIFICATE OF CORRECTION

PATENT NO.   :   5,262,007

DATED        :   November 16, 1993

INVENTOR(S)  :   Dean V. Phan, Bart S. Hersko

It is certified that error appears in the above-identified patent and that said Letters Patent is hereby corrected as shown below:

Column 2, line 47 "amonium" should read --ammonium--.

Column 2, line 54 "diester" should read --di-ester--.

Column 3, line 49 "diester" should read --di-ester--.

Column 8, line 6 "monoester" should read --mono-ester--.

Column 8, line 19 "monoesters" should read --mono-esters--.

Column 10, line 32 "1500 mi" should read --1500 mL--

Column 10, line 62 "anhydous" should read --anhydrous--.

Signed and Sealed this

Thirty-first Day of December, 1996

*Attest:*

BRUCE LEHMAN

*Attesting Officer*    Commissioner of Patents and Trademarks